United States Patent [19]

Parker et al.

[11] Patent Number: 5,041,554
[45] Date of Patent: Aug. 20, 1991

[54] ARYL-OR HETEROARYL-1-ALKYL-PYRROLE-2-CARBOXYLIC ACID COMPOUNDS USEFUL IN TREATING INTERLEUKIN-1 MEDIATED CONDITIONS

[75] Inventors: Roger A. Parker, Cincinnati; George Ku, West Chester, both of Ohio

[73] Assignee: Merrell Dow Pharmaceuticals Inc., Cincinnati, Ohio

[21] Appl. No.: 485,803

[22] Filed: Feb. 23, 1990

Related U.S. Application Data

[63] Continuation of Ser. No. 304,141, Jan. 31, 1989, abandoned.

[51] Int. Cl.$^5$ .......................................... C07D 207/325
[52] U.S. Cl. .................................. 548/532; 548/517; 548/518; 548/527
[58] Field of Search ................ 514/422, 423; 548/517, 548/518, 527, 532

[56] References Cited

U.S. PATENT DOCUMENTS

| | | | |
|---|---|---|---|
| 4,075,225 | 2/1978 | Rokach | 548/232 |
| 4,112,112 | 9/1978 | Rooney | 548/232 |
| 4,194,003 | 3/1980 | LaForest | 548/517 |
| 4,792,568 | 12/1988 | Auerbach | 548/527 |

OTHER PUBLICATIONS

G. De Martino, et al., *Il. Farmaco, Ed. Sci.* 28(12), 976–86(1973).
H. J. Anderson and S. J. Griffiths, *Canadian Journal of Chemistry*, 45, 2227–2232 (1967).
N. B. Mandava and W. J. Worley, *J. Nat. Prod.* 44, 94–100 (1981).
G. Kapadia and R. J. Highet, *Journal of Pharmaceutical Sciences* 57, 191 (1968).
Yves Girard, et al., *Journal of Organic Chemistry* 48, 3220–3224 (1983).
G. Cooper, et al., *Tetrahedron Letters No.* 45, 4321–4324(1971).
W. J. Irwin and D. L. Wheeler, *Tetrahedron Letters*, 28, 1113–1121(1972).
J. Rokach, et al., *Canadian Journal of Chemistry* 51, 3765–3770(1973).
M. Lennon, et al., *Journal of the Chemical Society, Perkin Trans, I.* 1(7), 622–626(1975).
D. A. Chirley, et al., *Journal of Organic Chemistry*, 20, 225–31(1955).
Niels Elming and Niels Clauson-Kaas, *Acta Chem. Scan.*, 6, 531–4(1952).
T. Reichstein, *Helv. Chem. Acta*, 13, 349–56(1930).

*Primary Examiner*—Donald G. Daus
*Attorney, Agent, or Firm*—William J. Stein

[57] ABSTRACT

This invention relates to novel aryl- or heteroaryl-1-alkyl-pyrrole-2-carboxylic acid compounds useful in treating interleukin-1 mediated conditions.

3 Claims, No Drawings

ARYL- OR HETEROARYL-1-ALKYL-PYRROLE-2-CARBOXYLIC ACID COMPOUNDS USEFUL IN TREATING INTERLEUKIN-1 MEDIATED CONDITIONS

CROSS-REFERENCE TO RELATED APPLICATION

This is a continuation of application Ser. No. 304,141, filed Jan. 31, 1989, now abandoned.

BACKGROUND OF THE INVENTION

Interleukin-1 refers to a family of molecules secreted by stimulated macrophages which effectuate multiple biological responses. The activities of interleukin-1 are summarized in Murphy, *British Journal of Rheumatology*, 24(suppl 1) 6-9, (1985), and Oppenheim et al., *Immunology Today*, 2, 45-55 (1986).

Interleukin-1 has been described to mediate T-lymphocyte proliferation and the acute phase response in inflammation. It also demonstrates pyrogenic and proinflammatory effects. Interleukin-1 induces connective tissue changes, and has been demonstrated to induce the release of degradative enzymes from mesenchymal cells that are present at the sites of bony erosion in inflammatory disease states such as rheumatoid arthritis. Billingham, *Brit. J. Rheumatology*, 24 (suppl 1), 25-28, (1985). Dayer, *Brit. J. Rheumatology*, 24 (suppl 1), 15-20, (1985). The production of acute phase proteins in hepatocytes during the acute phase of inflammation is mediated by IL-1. Whicher, *Brit. J. Rheumatology*, 24 (suppl 1), 21-24, (1985).

Interleukin-1 is also involved as a mediator in the inflammatory skin disease, psoriasis. Camp, et al., *J. Immunology*, 137, 3469-3474, (1986), and Ristwo, *Proc. Natl. Acad. Sci.*, USA 84, 1940-1944, (1987). It is cytotoxic for insulin producing beta cells in the pancreas, and is thus a causative factor in the development of some forms of diabetes myelitis. Bendtzen, et al., *Science*, 232, 1545-1547, (1986), and Marx, *Science*, 239, 257-258, (1988). Interleukin-1 also appears to be involved in the development of atherosclerotic lesions or atherosclerotic plaque. Marx, *Science*, 239, 2557-258, (1988). Interleukin-1 stimulates growth and proliferation of vascular smooth muscle cells, an effect which is greater in the absence or suppression of endogenous prostaglandins, which could lead to thickening of vascular walls such as occurs in atherogenesis. Libby, et al., *J. Clin. Invest.*, 81, 487-498, (1988).

It is therefore advantageous to control the release of interleukin-1 and interleukin-1-mediated conditions such as inflammation, psoriasis, diabetes, and atherosclerosis. Also, a need exists to control or treat interleukin-1 mediated inflammation without production of concomitant side effects which presently accompany the use of antiinflammatory steroids and non-steroidal antiinflammatory agents.

DESCRIPTION OF THE INVENTION

This invention relates to certain aryl- and heteroaryl-alkyl-pyrrole carboxylic acid compounds of the formula

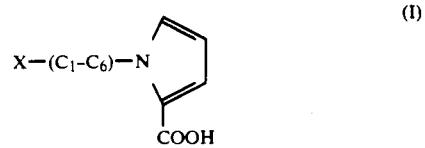

wherein
X is phenyl, naphthyl, or biphenyl (with the proviso that when X is unsubstituted phenyl, $C_1$–$C_6$ must be other than $C_1$ or $C_2$), each optionally substituted with one, two or three substituents selected from the group consisting of $C_1$–$C_4$ alkyl; or
X is thiophenyl or furanyl, each optionally substituted with a single substituent selected from the group consisting of $C_1$–$C_4$ alkyl, (with the proviso that when X is unsubstituted 2-furanyl, ($C_1$–$C_6$) must be other than $C_1$;
and to the salts thereof. The compounds of Formula I are useful as interleukin-1 inhibitors effective in alleviating interleukin-1 mediated conditions.

As used herein, the term ($C_1$–$C_6$) is used to describe straight or branched alkyl chains consisting of from one to six carbon atoms and which include such groups as methyl, ethyl, n-propyl, iso-propyl, n-butyl, iso-butyl, sec-butyl, tert-butyl, and the like.

The aryl or heteroaryl groups within the scope of this invention (X) can each be attached to the ($C_1$–$C_6$) chain at any available carbon atom on the aryl or heteroaryl ring. Additionally, when X is substituted with one, two or three substituent groups, the optional substituent(s) can be located at any available position on the ring. When X is substituted with more than one substituent, each substituent is selected independently of the other(s) so that the plurality of substituents may be the same or different.

The optional $C_1$–$C_4$ alkyl substituents refer to straight or branched chain alkyl groups having from one to four carbon atoms, and include such appropriate groups as described above for the ($C_1$–$C_6$) chain.

Illustrative examples of the compounds of this invention include:
1-(2-furanylmethyl)-1H-pyrrole-2-carboxylic acid;
1-(phenylmethyl)-1H-pyrrole-2-carboxylic acid;
1-([1,1'-biphenyl]-4-ylmethyl)-1H-pyrrole-2-carboxylic acid;
1-[3-(2-furanylpropyl)]-1H-pyrrole-2-carboxylic acid;
1-[6-(2-furanylhexyl)]-1H-pyrrole-2-carboxylic acid;
1-(2-naphthylmethyl)-1H-pyrrole-2-carboxylic acid;
1-[2-(2-thienylethyl)]-1H-pyrrole-2-carboxylic acid;
1-(3,5-dimethylphenylmethyl)-1H-pyrrole-2-carboxylic acid;
1-[2-(5-ethyl)furanylmethyl]-1H-pyrrole-2-carboxylic acid;
1-(3-furanylmethyl)-1H-pyrrole-2-carboxylic acid;
1-(5-phenylpentyl)-1H-pyrrole-2-carboxylic acid;
1-[(2,4,6-trimethyl)-phenylmethyl]-1H-pyrrole-2-carboxylic acid;
1-[2-(4,4'-dimethyl-1,1'-biphenyl-3-ylethyl)]-1H-pyrrole-2-carboxylic acid;
1-[4-(3,3'-dimethyl-1,1'-biphenyl-4-ylbutyl)]-1H-pyrrole-2-carboxylic acid;
1-[1-(2,7-dimethylnaphthylmethyl)]-1H-pyrrole-2-carboxylic acid;
1-[2-(3-[1,8-dimethyl]naphthylethyl)]-1H-pyrrole-2-carboxylic acid;

1-[3-(2-methyl)furanylmethyl]-1H-pyrrole-2-carboxylic acid;

1-[2-(3-methyl)thienylmethyl]-1H-pyrrole-2-carboxylic acid;

1-[4-(3-[2-methyl]thienylbutyl)]-1H-pyrrole-2-carboxylic acid;

1-[3-(2-ethyl)thienylmethyl]-1H-pyrrole-2-carboxylic acid;

1-[5-(3-[1-ethyl]naphthylpentyl)]-1H-pyrrole-2-carboxylic acid;

1-[2-(4-[2-ethyl]furanylethyl)]-1H-pyrrole-2-carboxylic acid;

1-[4-(3'-ethyl)-1,1'-biphenyl-4-ylbutyl]-1H-pyrrole-2-carboxylic acid;

1-[(4'-pentyl)-1-1'-biphenyl-4-ylmethyl]-1H-pyrrole-2-carboxylic acid;

1-[1-(2-hexyl)phenylmethyl]-1H-pyrrole-2-carboxylic acid;

1-(2-furanylethyl)-1H-pyrrole-2-carboxylic acid;

1-[1-(4-t-butyl)phenylmethyl]-1H-pyrrole-2-carboxylic acid.

As is true for most classes of therapeutically effective compounds, certain subclasses and certain species which are especially effective are preferred over others. In this instance, those compounds of Formula I wherein there is a one, two or three carbon chain between X and the pyrrole group, and X has no substituents are preferred. The most preferred compounds are those wherein X is an unsubstituted furanyl or unsubstituted biphenyl joined to the pyrrole ring by a methyl group.

The compounds of Formula I are produced by following the procedure set forth in Reaction Scheme 1.

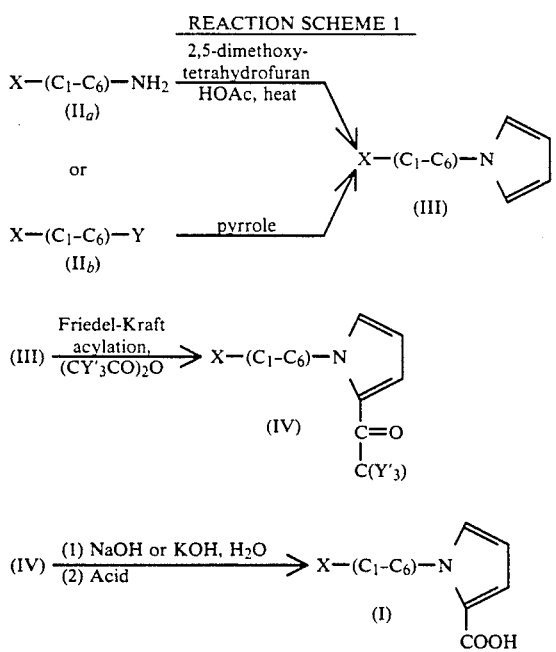

REACTION SCHEME 1 wherein X is as described for Formula I and Y and Y' are as described below.

In essence, Reaction Scheme 1 illustrates that the compounds of Formula I can be readily prepared by refluxing X-alkylamine (II$_a$) with 2,5-dimethoxytetrahydrofuran and glacial acetic acid to produce X-alkyl-pyrrole (III), or by reacting pyrrole (in dimethylacetamide) with X-(C$_1$-C$_6$)-Y (II$_b$), (where Y is chlorine, bromine or iodine, or mesylate or tosylate) to produce III which is then converted to the acetyl-pyrrole compound IV by means of standard Friedel-Krafts acylation with (CY'$_3$CO)$_2$O (where Y' can be fluorine, chlorine, or bromine), and then refluxing IV with sodium hydroxide (NaOH) or potassium hydroxide (KOH) and water and finally acidifying the compound with an acid such as malonic acid, hydrochloric acid or acetic acid, to yield the compounds of Formula I.

The following specific examples are presented to illustrate the synthesis of the compounds of this invention, but they should not be construed as limiting the scope of this invention in any way.

EXAMPLE 1

1-(2-Furanylmethyl)-1H-Pyrrole-2-Carboxylic Acid

Furfurylamine (5.0 g, 51.5 mMol), 2,5-dimethoxytetrahydrofuran (6.8 g, 51.5 mMol), and 50 ml of glacial acetic acid were placed in a 100 ml round bottom flask equipped with a reflux condenser. The flask was heated to reflux for 1½ hours, then evaporated to dryness under reduced pressure to give 8.5 g of a dark oil. The oil was distilled in a Kugelrohr apparatus and the fraction collected at 50° C. to 70° C. at 0.1 mm Hg pressure gave 4.9 g 1-furfurylpyrrole as an oil.

1-Furfurylpyrrole (2.3 g, 15.6 mMol), 15 ml of trifluoroacetic anhydride (22.35 g, 106 mmol), 50 ml of nitromethane and 25 ml anhydrous diethylether were combined in a 100 ml round bottom flask. The mixture was stirred overnight under positive argon. The reaction was heated and the excess solvents distilled off. The mixture was evaporated to dryness under reduced pressure to give 3.9 g of a dark oil. The oil was distilled in a Kugel-rohr apparatus. The fraction collected at 80° C. to 90° C. at 0.2 mm Hg pressure gave 3.0 g of the colorless oil. 1-(2-furanylmethyl)-2-trifluoroacetyl-1H-pyrrole. This oil was combined with 50 ml ethylalcohol in a 100 ml round bottom flask equipped with a reflux condenser. The mixture was heated to reflux. Sodium hydroxide, 3.0 g in 15 ml of water, was added, and the reaction mixture was refluxed for 3 hours. The ethanol was distilled off and 50 ml of water was added. The mixture was cooled and acidified by addition of 5.0 g malonic acid. A precipitate formed which was collected by filtration. The solid precipitate was recrystallized from acetonitrile to give the title compound a white powder, mp =117° C. to 118° C., infrared spectrum absorption at 3400 cm$^{-1}$, 1675 cm$^{-1}$, 1530 cm$^{-1}$, 1440 cm$^{-1}$, 720 cm$^{-1}$.

In like manner, by substituting the following starting materials for furfurylamine above, and following the procedure in Example 1, the following compounds are made:

1. Start with 3-furfurylamine (or 3-furanylmethylamine) to yield 1-(3-furanylmethyl)-1H-pyrrole-2-carboxylic acid.

2. Start with 2-thiophenemethylamine to yield 1-(2-thienylmethyl)-1H-pyrrole-2-carboxylic acid.

3. Start with 4-methyl-2-thiophenemethylamine to yield 1-[2-(4-methyl)thienylmethyl]-1H-pyrrole-2-carboxylic acid.

4. Start with 3-(3-furanylpropyl)amine to yield 1-[3-(3-furanylpropyl]-1H-pyrrole-2-carboxylic acid.

5. Start with 4-methyl-2-furanylmethylamine to yield 1-[2-(4-methyl)furanylmethyl]-1H-pyrrole-2-carboxylic acid.

EXAMPLE 2

1-(Phenylmethyl)-1H-Pyrrole-2-Carboxylic Acid

Benzylamine (10.7 g, 0.1 mol), 2,5-dimethoxytetrahydrofuran (13.2 g, 0.1 mol), and 50 ml of glacial acetic acid were combined in a 100 ml round bottom flask equipped with a reflux condenser. The reaction was heated to reflux for 2 hours, then evaporated to dryness under reduced pressure on a rotoevaporator to give 18.0 g of an oily residue. The oil was distilled in a Kugelrohr apparatus at 85° C. to 120° C. (0.25 mm Hg) pressure to give 11.5 g (73%) of 1-benzyl-1H-pyrrole.

1-Benzyl-1H-pyrrole (3.1 g, 20 mMol), trichloroacetic anhydride (7.4 g, 24 mMol) and 50 ml of anhydrous ether (diethylether) in a 100 ml round bottom flask were allowed to stand at room temperature overnight, then the mixture was evaporated to dryness under reduced pressure to give 5.0 g of 1-benzyl-2-trichloroacetyl-1H-pyrrole as a yellow oil. The 5.0 g of oil was combined with 100 ml of ethanol (ethyl alcohol) in a 250 ml round bottom flask. The mixture was heated to reflux then sodium hydroxide (3.0 g) in 15 ml of water was added. The reaction refluxed for 2 hours and was then diluted with 50 ml water. The mixture was cooled in an ice-bath then acidified by addition of 5.0 g of malonic acid. The mixture was then extracted with diethylether in a 500 ml seperatory funnel. The ether layer was washed with water and saturated sodium chloride solution (brine). The ether layer was filtered through sodium sulfate and evaporated to dryness under reduced pressure to give 2.8 g of a brown crystalline solid. The solid was recrystallized from acetonitrile to give 1.3 g of white fluffy crystals of the title compound. mp = 130° C. to 133° C.

In like manner, by substituting the following starting materials for benzylamine above, and following the procedure in Example 2, the following compounds can be made:

1. Start with 3-phenyl-1-propylamine to yield 1-(3-phenylpropyl)-1H-pyrrole-2-carboxylic acid.
2. Start with p-butylbenzylamine to yield 1-[(4-butyl)-phenylmethyl)-1H-pyrrole-2-carboxylic acid.
3. Start with o-hexylbenzylamine to yield 1-[1-(2hexyl)-phenylmethyl]-1H-pyrrole-2-carboxylic acid.

EXAMPLE 3

1-([1-1'-Biphenyl]-4-methyl)-1H-Pyrrole-2-Carboxylic Acid

Pyrrole (3.4 g, 51 mmol), 2.0 g of 60% sodium hydride in oil (51 mMol) and 50 ml of dimethylacetamide were combined in a 100 ml round bottom flask and stirred at room temperature for 2 hours. Para-phenylbenzyl chloride (10.1 g, 50 mMol) was added to the reaction mixture and the reaction stirred overnight at room temperature. The reaction mixture was then heated in a steam bath for 2 hours, and the mixture cooled and diluted with water and diethylether. The layers were separated in a 500 ml seperatory funnel. The ether layer was washed with water and the filtered through sodium sulfate, then evaporated to dryness under reduced pressure to give 12.2 g of a solid mixture. The mixture was crystallized from acetonitrile to give 5.7 g of starting phenylbenzyl chloride. Evaporation of the remaining liquid under reduced pressure gave 6.5 g of the semi solid.

The 6.5 g of 1-(p-phenylbenzyl)-1H-pyrrole in 50 ml diethylether was combined with 10 ml trichloroacetic anhydride in a 100 ml round bottom flask, and allowed to stand at room temperature overnight. Then the mixture was evaporated to dryness under reduced pressure to give a residue. The residue was dissolved in 200 ml ether, and the ether layer was washed with saturated sodium bicarbonate solution and brine. The ether layer was filtered through sodium sulfate and evaporated to dryness to give 9.0 g of a dark oil.

The oil, in 100 ml of ethanol, was heated to reflux and sodium hydroxide ,(5.0 g) in 25 ml of water, was added. The reaction was refluxed for 2 hours, cooled, and acidified with 5.0 g of malonic acid. The precipitate was extracted into ether and the ether evaporated to dryness to give 7.2 g of a tan powder. The powder was recrystallized from acetonitrile to give 4.2 g of the title compound as a light tan powder. mp = 190° C.

In like manner, by substituting the following starting materials for p-phenylbenzyl chloride above, and following the procedure in Example 3, the following compounds can be made:

1. Start with 2-naphthylmethylchloride to yield 1-(2-naphthylmethyl)-1H-pyrrole-2-carboxylic acid.
2. Start with 4-[(1,1'-biphenyl)-4-yl]-butyl bromide to yield 1-[4-([1,1'-biphenyl]-4-yl)butyl]-1H-pyrrole-2-carboxylic acid.
3. Start with 5-phenylpentyl bromide to yield 1-(5-phenylpentyl)-1H-pyrrole-2-carboxylic acid.
4. Start with 4'-methyl-1,1'-biphenyl-4-yl-methylchloride to yield 1-(4'-methyl-1,1'-biphenyl-4-ylmethyl)-1H-pyrrole-2-carboxylic acid.
5. Start with 1-methyl-2-naphthylmethylchloride to yield 1-(1-methyl-2-naphthylmethyl)-1H-pyrrole-2-carboxylic acid.

The compounds of this invention are useful both in the free acid form and as salts. The expression "pharmaceutically-acceptable salt" means any organic or inorganic addition salt of the compounds of Formula I which are relatively non-toxic and innocuous to a patient at concentrations consistent with effective activity so that the side effects ascribable to the salt do not vitiate the beneficial effects of the base compounds of Formula I. These salts are included within the scope of this invention. Such salts include ammonium salts; alkali metal salts, such as sodium and potassium salts; alkaline earth metal salts, such as the calcium and magnesium salts; salts with organic bases such as, for instance, dicyclohexylamine salts, N-methyl-D-glucamine, and salts with amino acids such as arginine and lysine; and the like. The non-toxic, physiologically acceptable salts are preferred, although other salts are also useful, for, for example, isolating or purifying the product, or for use as tools in research.

The salts are formed by conventional means such as by reacting the free acid forms of the product with one or more equivalents of the appropriate base in a solvent or medium in which the salt is insoluble, or in a solvent such as water which is then removed in vacuo or by freeze-drying, or by exchanging the cations of an existing salt for another cation on a suitable ion exchange resin.

The compounds of Formula I are interleukin-1 inhibitors effective in alleviating interleukin-1 mediated conditions. Typically, they are administered to a mammal in need of control of interleukin-1 secretion, control of interleukin-1-mediated effects, or control of interleukin-1-mediated inflammation, in an amount effective to produce an interleukin-1 response. A response is a measurable effect produced as a result of the administration of the compound. The compounds are administered to inhibit or treat interleukin-1-mediated conditions such a inflammation, psoriasis, atherosclerosis, and diabetes.

The interleukin-1 inhibitory properties of the compounds of this invention can readily be determined by standard and well known procedures. For example, the following procedure was utilized to demonstrate interleukin-1 inhibitory activity.

Peritoneal cells from mice which had been orally dosed with 100 mg/kg of test compound 40, 24 and 16 hours prior to sacrifice, were collected by lavage, pooled and washed by centrifugation. The cells were resuspended in RMPI-1640 medium containing antibiotics, and plated. After 1 hour of incubation at 37° C., non-adherent cells were removed, and RMPI, with or without lipopolysaccharide, was added to each well. The presence of lipopolysaccharide will induce interleukin-1 secretion by macrophages. After incubation for 6 hours, the culture supernatant was collected, filtered and stored until assayed.

Mouse thymocytes were suspended in RPMI enriched with fetal bovine serum and 2-mercaptoethanol. Aliquots of cell suspension were incubated with an equal volume of dilutions of macrophage culture supernatant in the presence of a suboptimal amount of phytohemagglutinin for 72 hours in flat-bottom plates. Microcultures were pulsed with $H^3$-thymidine for the last 16 hours and were harvested on glass fiber filters. $H_3$-thymidine will be incorporated into the DNA of actively proliferating cells. The radioactivity was determined by liquid scintillation counting, and interleukin-1 activity was expressed in units defined as the reciprocal of the dilution required to give 50% of maximal $H^3$-thymidine incorporation.

The effects of the compounds of Formula I as interleukin-1 inhibitors is presented in Table I.

TABLE 1

| Compound | ExVivo Inhibition of Interleukin-1 Secretion by Macrophages | |
|---|---|---|
| | Interleukin-1 units/ml Mean ± Sem(n) | % Inhibition |
| 1 | 10.2 +/− 3.4 | 93.2 |
| control | 149.4 +/− 35.5 | |
| 2 | 171.3 +/− 7.9 | 67.4 |
| control | 526.1 +/− 65.5 | |
| 3 | 26.6 +/− 3.9 | 94.9 |
| control | 526.1 +/− 65.5 | |

Compounds were administered at a dosage of 100 mg/kg, p.o. 3 times (40, 24 and 16 hours prior to sacrifice).
Compound 1: 1-(2-furanylmethyl)-1H-pyrrole-2-carboxylic acid
Compound 2: 1-(phenylmethyl)-1H-pyrrole-2-carboxylic acid
Compound 3: 1-([1,1'- biphenyl]-4-ylmethyl)-1H-pyrrole-2-carboxylic acid The above results indicate that significant inhibition of interleukin-1 release was obtained with the test compounds.

A patient, for the purpose of this invention, is a mammal, including a human, in need of treatment for a particular condition, injury or disease. The amount of active ingredient (i.e., a compound of Formula I) to be administered to a patient for the treatment of interleukin-1 mediated conditions can vary widely according to such considerations as the particular dosage unit employed, the period of treatment, the age and sex of the patient treated, and the nature and extent of the condition to be treated.

The compounds of this invention are utilized to achieve the desired pharmacological effect by administration to a patient in need thereof in an appropriately formulated pharmaceutical composition, using conventional dosage unit forms parenternally, orally, topically, or the like.

The total amount of active ingredient to be administered intravenously generally ranges from about 0.1 mg/kg to 30 mg/kg and preferably from 1.0 mg/kg to 10.0 mg/kg. A unit dosage may contain from 5 to 525 mg of active ingredient, and can be taken one or more times per day. For example, a 50 kg patient may be administered 50 mg to 700 mg active ingredient four times a day for a total dose of 200 to 2800 mg per day.

The total amount of active ingredient to be administered orally generally ranges from 0.1 mg/kg to 100 mg/kg, and preferably from 1.0 mg/kg to 50 mg/kg. A unit dosage may contain from 5 to 1000 mg of active ingredient, and can be taken one or more times per day. For example, a 50 kg patient may be administered 50 to 2500 mg of active ingredient four times a day for a total of 200 to 10,000 mg per day.

The total amount of active ingredient present in a topical formulation generally ranges from 0.01% to 15% (weight/vol.) of the pharmaceutical composition. The preferable amount of active ingredient is from 1% to 10% (weight/vol.) of the pharmaceutical composition. Generally, a topical composition may be administered one or more times per day, or it may be administered as a sustained release preparation where the active ingredient from a single dose is released over one or more days.

For oral administration the compounds are formulated into solid or liquid preparations such as capsules, pills, tablets, troches, lozenges, melts, powders, solutions, suspensions, or emulsions and may be prepared according to any method known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment, the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention are also administered parenternally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3- dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin or cetyl alcohol. The sterile injectable preparation may also be a sterile injectable solution or suspension in a non-toxic parenternally-acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

The compounds of this invention may also be administered topically, that is, by means of external application to the skin or mucous membranes, through formulation as an ointment, cream, lotion, gel, jelly, dressing, plaster, powder, poultice, or paste. Formulation of topical compositions of compounds of this invention may be accomplished by following standard and accepted procedures such as those described in *Remington's Pharmaceutical Sciences.* 16th Ed. 1980, Arthur Osol, Editor, Mack Publishing Company, Easton, Pa.

The compositions of the invention can also contain other conventional pharmaceutically-acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The following specific examples are presented to illustrate compositions of this invention, but they should not be construed as limiting the scope of this invention in any way.

EXAMPLE 4

A tablet is prepared from:

| | |
|---|---|
| 1-(2-Furanylethyl)-1H-Pyrrole-2-Carboxylic Acid | 250 mg |
| Starch | 40 mg |
| Talc | 10 mg |
| Magnesium Stearate | 10 mg |

EXAMPLE 5

A capsule is prepared from:

| | |
|---|---|
| 1-[1-(4-t-butyl)-phenylmethyl]-1H-Pyrrole-2-Carboxylic Acid | 400 mg |
| Talc | 40 mg |
| Sodium Carboxymethyl Cellulose | 40 mg |
| Starch | 120 mg |

EXAMPLE 6

A cream is prepared from:

| | |
|---|---|
| 1-([1-1'-Biphenyl]-4-ylmethyl)-1H-Pyrrole-2-Carboxylic Acid | 4.0 g |
| Cetyl Alcohol | 7.0 g |
| Gylcerol Monostearate PEG 40 | 8.0 g |
| Diglycol Stearate | 6.0 g |
| Polyethylene Glycol 400 | 37.5 g |
| Purified Water | 37.5 g |

The nonaqueous phase ingredients were combined and heated with stirring to 60° C. and the compound of this invention was added and mixed until dispersed or dissolved. Purified water was heated to 60° C. and added to the nonaqueous phase with agitation. The resulting emulsion was cooled to room temperature with continued agitation.

The compounds of Formula I may also be utilized, in free acid form or in compositions, as tools in research and diagnostics or as analytical references or standards and the like. Therefore, the present invention includes compositions which are comprised of an inert carrier and an effective amount of a compound of Formula I, or a salt thereof. An inert carrier is any material which does not interreact with the compound to be carried and which lends support, means of conveyance, bulk, traceable material, and the like to the compound to be carried. An effective amount of compound is that amount which performs in a desirable manner or produces a result or exerts an influence on the particular procedure being performed.

It should be apparent to one of ordinary skill in the art that changes and modifications can be made to this invention without departing from the spirit or scope of the invention as it is set forth herein.

What is claimed is:

1. A compound of the formula

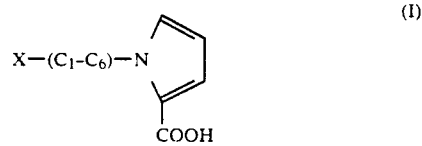

wherein X is biphenyl, optionally substituted with one, two or three substituents selected from the group consisting of $C_1$–$C_4$ alkyl and the pharmaceutically acceptable salts thereof.

2. A compound of claim 1 wherein the ($C_1$–$C_6$) chain is a saturated chain having one, two or three carbon atoms.

3. A compound of claim 1 which is [1-([1,1'-biphenyl]-4-ylmethyl)-1H-pyrrole-2-carboxylic acid] 1-([1,1'-biphenyl]-4-methyl)-1H-pyrrole-2-carboxylic acid.

* * * * *